United States Patent [19]

Chandler

[11] Patent Number: 4,791,060

[45] Date of Patent: Dec. 13, 1988

[54] DEVICE FOR PERFORMING QUALITATIVE ENZYME IMMUNOASSAYS

[75] Inventor: Howard M. Chandler, Orton, Canada

[73] Assignee: Allelix Inc., Mississauga, Canada

[21] Appl. No.: 933,171

[22] Filed: Nov. 21, 1986

Related U.S. Application Data

[63] Continuation-in-part of Ser. No. 551,906, Nov. 15, 1983, Pat. No. 4,665,034.

[51] Int. Cl.[4] .................. C12M 1/00; C12M 1/24; G01N 1/48; G01N 33/544
[52] U.S. Cl. ..................... 435/296; 435/287; 435/810; 426/535; 426/808; 426/818; 422/57; 422/58; 422/61; 422/68; 422/100
[58] Field of Search ............... 435/296, 806, 7, 810, 435/287; 436/535, 808, 818; 422/57, 58, 99, 61, 68, 69, 71, 100

[56] References Cited

U.S. PATENT DOCUMENTS

| | | | |
|---|---|---|---|
| Re. 31,006 | 8/1982 | Schuurs et al. | 435/7 |
| 4,276,048 | 6/1981 | Leaback | 435/296 |
| 4,585,623 | 4/1986 | Chandler | 435/296 |
| 4,665,034 | 5/1987 | Chandler | 435/287 |

FOREIGN PATENT DOCUMENTS

WO-82/02211  7/1982  PCT Int'l Appl. .
WO-83/01119  3/1983  PCT Int'l Appl. .

*Primary Examiner*—Benoit Castel
*Attorney, Agent, or Firm*—Ridout & Maybee

[57] ABSTRACT

The invention relates to a device and method for performing qualitative enzyme immunoassays. The device comprises at least one tube having antibody, antigen or hapten attached to an internal surface thereof. A first syringe is connectable to a first end of the tube or tubes and supplies a flow of test liquid therethrough. A second syringe having a two piston arrangement is connected to the tube so as to allow a first wash solution followed by an enzyme conjugate solution to be flowed therethrough. Finally a third syringe, also having a two piston configuration, is connected to the tube so as to allow a second wash solution followed by an enzyme substrate and metabolite indicator solution to be flowed therethrough.

14 Claims, 4 Drawing Sheets

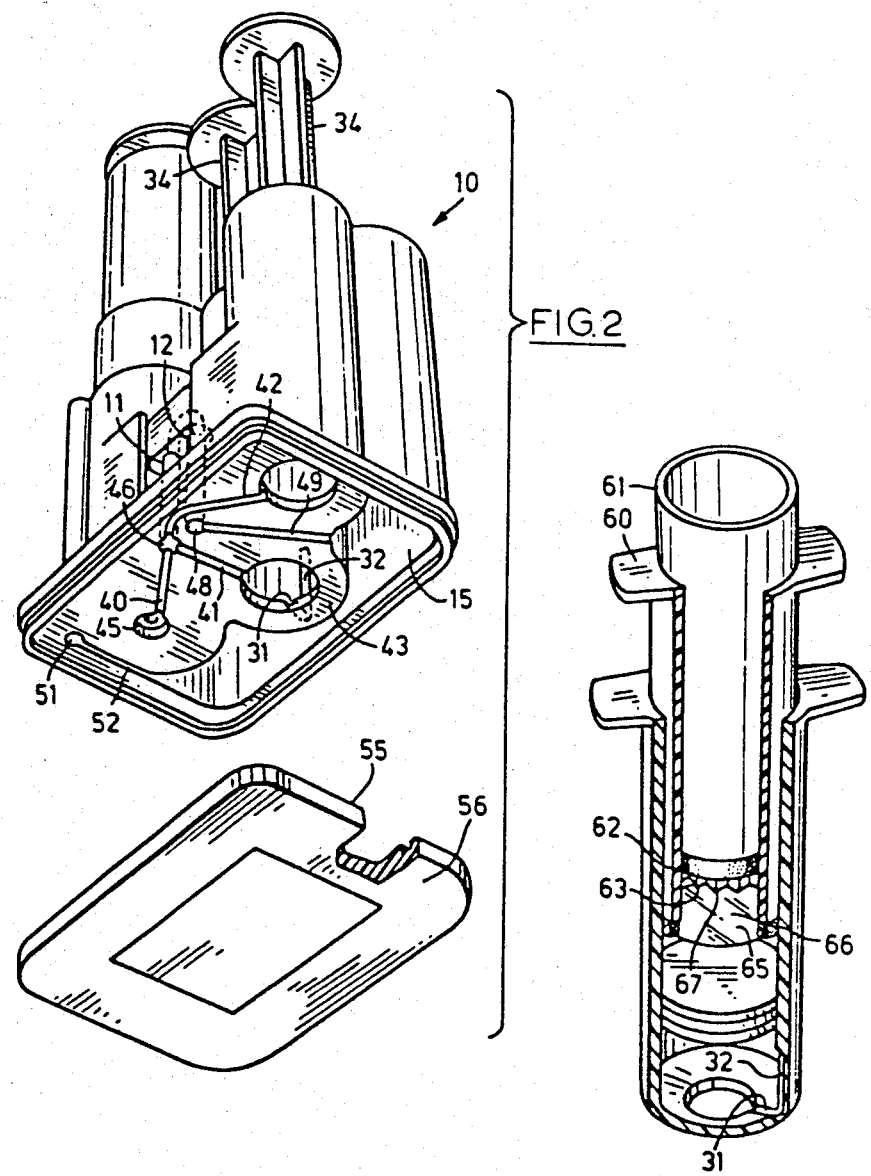

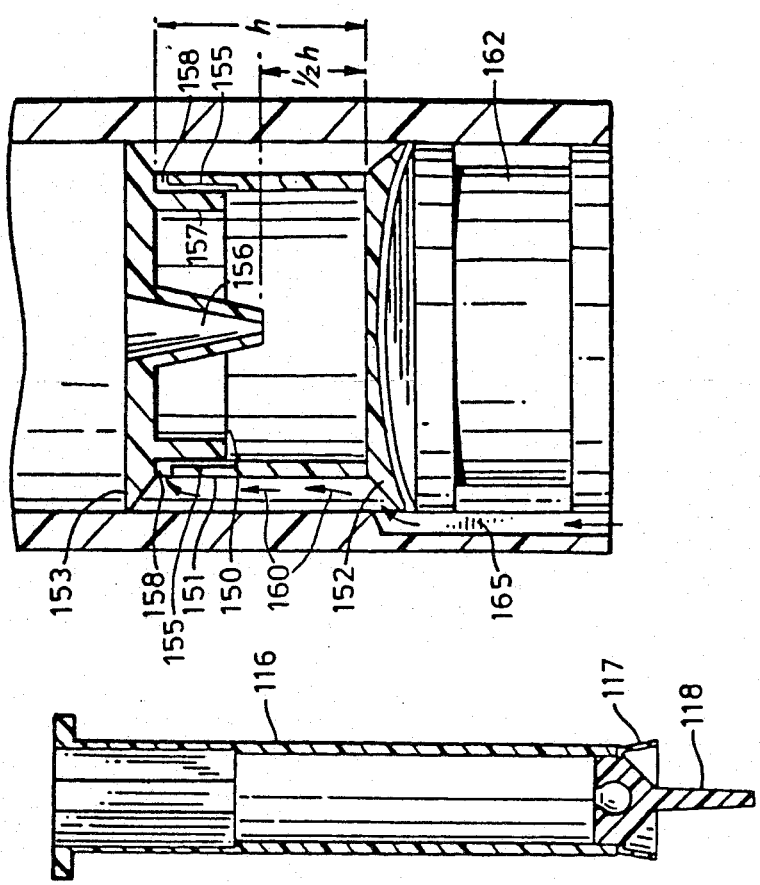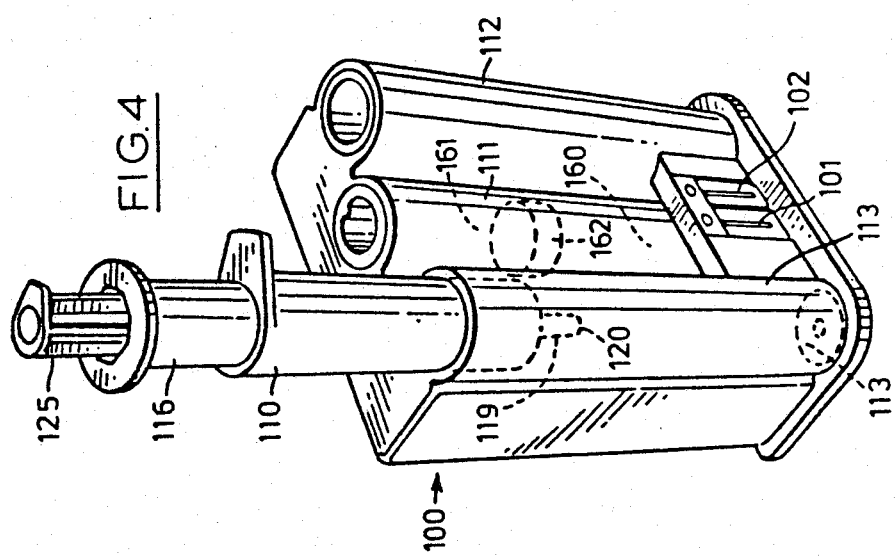

DEVICE FOR PERFORMING QUALITATIVE ENZYME IMMUNOASSAYS

BACKGROUND OF THE INVENTION

This application is a continuation-in-part of application Ser. No. 551,906 filed Nov. 15, 1983 now U.S. Pat. No. 4,665,034.

The present invention relates to a device for performing qualitative enzyme immunoassays. The invention provides a portable compact device which may be used by an untrained person or which is suitable for use by medical personnel in the field or elsewhere when a quick determination is required for diagnostic purposes. The device is particularly suitable for testing urine samples but also may be used for performing enzyme immunoassays using a wide variety of test solutions.

In its preferred form, the invention may be used to detect the presence of an antigen or hapten in urine or serum. This assay is accomplished by the known method of contacting the sample with an antibody specific to the antigen or hapten being assayed for, which antibody is attached to a solid support such as the wall of a tube. Antigen which is captured by the fixed antibody is then detected by contacting the solid phase with an antibody/enzyme conjugate followed by treatment with an enzyme substrate and suitable indicator.

The present device is capable of detecting the substance being assayed for in lower concentration and with much greater speed than has heretofore been possible with prior art devices. Prior devices for the detection of an antigen or hapten employ an antibody attached to a solid support which is contacted sequentially with static volumes of test liquid, conjugate and substrate/indicator solutions. A period of incubation must be observed for each of these contacting steps as the reactions involved are diffusion controlled. That is, the reactions take place only at the surface of the solid support and sufficient time must elapse to enable enough antigen to migrate to the reaction vessel wall to give a positive test result. Increasing the surface area to volume ratio by carrying out these reactions in a tube having a small bore reduces incubation periods to about ten minutes each.

The present device employs a method whereby a continuous flow of the various reactive solutions are passed through a tube having the antibody affixed thereto so that the principles of affinity capture and concentration are utilized. That is, the reaction at the tube wall is forced to completion quickly by continuously bathing the solid reactant with a solution having a constant concentration of the co-reactant. This also means that the sensitivity of the assay is increased since a much lower concentration of co-reactant in the test sample can be detected by this flow through method. Thus, the present invention provides significant advantages over the devices and methods previously known. In the case of a pregnancy test, discussed in detail below, the assay for the presence of human chorionic gonadotropin (HCG) in the urine may be carried out as quickly as about three minutes using the device of the invention as compared to prior art pregnancy test devices which require 20 to 120 minutes to perform the assay. Also, the present device is much simpler to use than prior devices and many fewer operations need be performed when using the device in order to carry out the assay than is required by prior devices.

It should also be clear that the present device may be used generally for all enzyme immunoassays and should not be construed as being restricted to the detection of antigens or haptens in the manner just summarized. Without limiting the possible applications of the present invention, the device may be used as suggested to detect antigen or hapten in an antibody sandwich-type assay, or a double antibody sandwich antigen assay may be used, or a competitive antigen assay can be performed. When detection of antibody is desired, the device can be used to do a sandwich-type assay or a double antibody sandwich antibody assay. For example, in an antigen assay for ± hepatitis subunit or virus using the double antibody sandwich antigen assay, the solid phase comprises anti-hepatitis Ab type 1 (e.g. sheep), the second antibody used is anti-hepatitis Ab type 2 (e.g. rabbit), and the conjugate is anti-type 2 Ab/enzyme.

The present device is especially suitable if a large volume of test sample (e.g. 5 to 10 ml) is available, such as urine. A particularly suitable assay using the present device is a test for the presence of HCG (human chorionic gonadotropin) in urine to determine pregnancy. Because of the aforementioned features, pregnancy can be quickly detected at an early stage by the woman herself using the present device.

SUMMARY OF THE INVENTION

Accordingly, the invention provides a device for performing an enzyme immunoassay, comprising at least one assay tube having an antibody, antigen or hapten attached to an internal surface thereof. A first syringe is connectable to a first end of said tube or tubes for supplying a flow of test liquid therethrough, and a second syringe is connected to the first end of the assay tube for supplying a flow of a first wash solution followed immediately by a flow of enzyme conjugate containing solution therethrough, said second syringe having a first unattached piston and a second piston which may be directly depressed by a plunger, the first piston being positioned to separate the first wash solution from the conjugate solution, and said second syringe also having a wall with a groove therein connecting the syringe outlet with the conjugate solution only when the first piston is fully depressed. A third syringe is connected to the first end of the assay tube for supplying a flow of a second wash solution followed immediately by a flow of solution containing enzyme substrate and enzyme metabolite indicator therethrough, said third syringe having a structure like that of the second syringe. Alternatively, the third syringe may comprise a syringe insert positioned in the upper portion thereof for containing substrate solvent. The insert has a tip which is insertable into a cavity formed in the top of the first piston. A space is defined between the end of the insert and the top of the first piston for containing powdered substrate.

BRIEF DESCRIPTION OF THE DRAWINGS

A preferred embodiment of the invention will be described with reference to the drawings in which:

FIG. 2 is a perspective view from below the device with the bottom plate removed;

FIG. 3 is a cut away view of an alternate double piston syringe which may be used in the present device;

FIG. 4 is a perspective view of a second preferred embodiment of the device;

FIG. 5 is a sectional view of a modified plunger for the sample syringe;

FIG. 7 shown on the same sheet as FIG. 5, is a sectional detail view showing a modified upper piston for the second or conjugate containing syringe.

DESCRIPTION OF THE PREFERRED EMBODIMENTS

Figure 1:
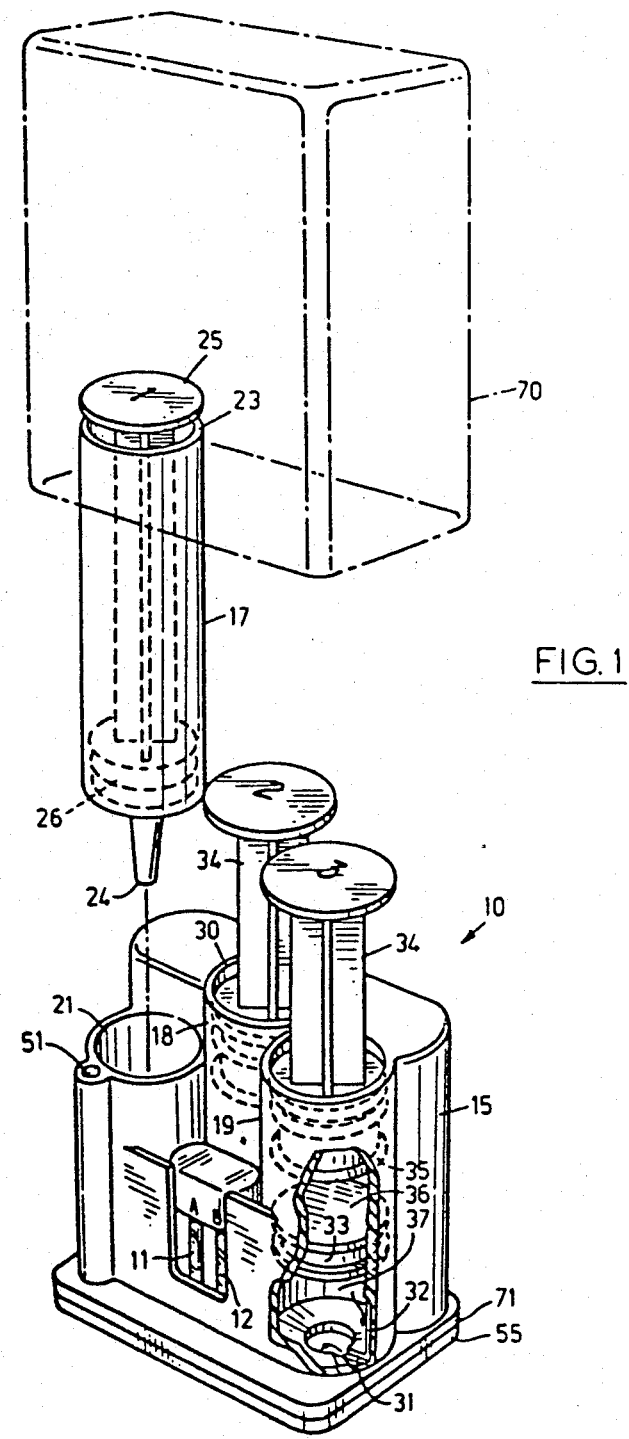
FIG. 1 is a perspective view partially cut away of the testing device.

While the present device may be used for a number of different assay applications, and indeed may be used for performing multiple assays on a single test sample, the preferred embodiment hereinafter described relates to the use of the invention for testing for pregnancy by assaying for the presence of HCG (human chorionic gonadotropin) in urine.

The preferred testing device of the invention comprises a body 10 in which is centrally disposed an assay tube 11 having applied to the inner wall thereof a coating of anti-HCG, i.e. HCG antibody. The anti-HCG coating is preferably covalently bonded to the tube wall, but it may be affixed by adsorption. For the purpose of providing a control, the assay tube 11 is connected in series to a plain uncoated tube 12. The control tube 12 is in turn connected to a waste reservoir 15 as described below. In order to make good use of the advantages of the flow through technique, it is desirable to have a surface area to volume ratio in the tube 11 as large as is practical given the various parameters surrounding the manufacture and use of the preferred device. Thus, an assay tube 11 on the order of about 25 mm in length having a bore of about 1 mm in diameter is quite suitable in the present context.

The various solutions required to perform the assay are passed sequentially through the tubes 11 and 12 by means of first, second and third syringes 17, 18 and 19. A test sample syringe 17 is removable from a receptacle 21 therefor which is integral with the body 10. The test sample syringe 17 comprises a body 23 having an outlet 24 at one end and a plunger 25 having a piston 26 attached at an end thereof which may move slidably within the syringe body 23 to fill and empty the syringe 17 with a liquid test sample. A urine sample of about 5 ml is reasonable for use in the particular pregnancy test device described herein.

The body 10 preferably has two additional syringes 18 and 19 integral therewith. However, a device of the invention may comprise removable syringes 18 and 19, and indeed this may be desirable in certain circumstances. The syringe 18 comprises a receptacle 30 having an outlet 31 at its lower end and a groove 32 communicating with the outlet 31 in the wall thereof. The syringe receptacle 30 is provided with an unattached piston 33 and a plunger 34 having a piston 35 attached at one end thereof. The free piston 33 is used to separate two solutions contained within the syringe receptacle 30, one solution contained in an upper portion 36 of the syringe 18 between the free piston 33 and the plunger 34, and the other solution contained in a lower portion 37 between the free piston 33 and the outlet 31. The final syringe 19 is of a structure identical to that of syringe 18.

The outlets of the syringes 17, 18 and 19 are connected to the lower end of the assay tube 11 by means of channels 40, 41 and 42 formed in the base 43 of the body 10 (FIG. 2). The channel 40 connects an opening 45 for the outlet 24 of the sample syringe 17 to an opening 46 for the tube 11. Likewise channels 41 and 42 connect the outlets 31 of syringes 18 and 19 with the opening 46. An opening 48 is provided in the base 43 for the outlet end of the control tube 12 which is in turn connected to the waste reservoir 15 by means of a channel 49. Finally, a vent shaft 51 is provided in the body 10, the lower end of which is connected to the waste reservoir 15 by means of a slot 52 in the body 10. The base 43 comprises a flat surface which fits flush against an unbroken flat surface 55 of a bottom plate 56 for the device. The surface 55 coacts with the grooves formed in the base 43 to form the channels 40, 41 and 42.

For the purpose of providing a pregnancy testing device, the syringe 18 is filled with a solution containing an enzyme/anti-HCG conjugate in the upper portion 36. A urease/anti-HCG conjugate is preferred in this regard. The lower portion 37 of the syringe 18 is filled with a wash solution compatible with the subsequently added conjugate solution.

The upper portion 36 of the syringe 19 is filled with a solution containing substrate for the enzyme of the conjugate and an indicator to detect the conversion of substrate by the enzyme in the assay tube 11. Preferably, the substrate is urea which is metabolized by the urease of the conjugate to give ammonia and carbon dioxide. The pH rise caused by the release of ammonia can then be detected by a pH indicator such as bromthymol blue. The lower portion 37 of the syringe 19 is filled with a suitable wash solution, which in the particular device described herein is the same as in the syringe 18.

To operate the present device to determine a suspected pregnancy, the syringe 17 is filled with a urine sample and inserted into the receptacle 21. With the syringe 17 in place in the device, the plunger 25 is slowly depressed so that the urine sample flows through the tubes 11 and 12 over a period of about one minute. Next, the plunger 34 of the syringe 18 is fully depressed causing a first wash solution to flow through the tubes 11 and 12 thereby washing out retained urine sample, and then causing a flow of enzyme/antibody conjugate solution to pass through the tubes 11 and 12. An incubation period of about two minutes should be observed at this point to allow the conjugate time to react with any HCG captured by the anti-HCG held at the assay tube 11 wall. If required, a longer incubation period may be used to increase the sensitivity of an assay.

After the incubation period has elapsed, the plunger 34 of the syringe 19 is fully depressed causing a second wash solution to flush the conjugate from the tubes 11 and 12, and then causing a flow of substrate/indicator solution to pass through the tubes 11 and 12. If the woman is pregnant and therefore, HCG is therefore present, the captured enzyme in the assay tube 11 will metabolize the substrate and cause the indicator to be activated. Use of a color change indicator such as bromthymol blue in a urea/urease system will give a change in the color of the liquid in the assay tube 11 from yellow to blue. This color change can be compared with the color in the control tube 12 which should remain yellow. A relatively high concentration of HCG in the test sample will give a color indication almost immediately, however, a low concentration of HCG will require up to 10 minutes to give a positive indicator response.

Because of the aforementioned features of the present device, low levels of HCG on the order of 50 mIU/ml can be detected. This is important so that pregnancy can be diagnosed at an early stage, and so that a quick test can be carried out to reliably indicate an ectopic pregnancy.

The preferred enzyme for use in the pregnancy test device of the invention is urease because it is easily detected by the pH rise caused by metabolism of its substrate urea. Also, urea is stable in aqueous solution for at least six months at room temperature. This is in contrast to other substrates such as hydrogen peroxide, used with horseradish peroxidase, which breaks down rather quickly. However, without refrigeration, urea in water will eventually break down thereby making the device unusable. To provide a device having a long shelf life, i.e. two years, at room temperature, the syringe 19 may be modified as shown in FIG. 3.

The modified syringe 19 has a hollow plunger 60 equipped with a rod 61 slidably disposed longitudinally within it. The rod 61 has a piston 62 affixed at its lower end, and the piston 62 has a piercing member 63 protruding from the lower surface thereof. The plunger 60 has a rupture membrane 65 covering the opening at its lower end, and the chamber 66 created by the membrane 65, the interior of the plunger 60 and the lower end of the rod 61 provides a space for storing powdered urea or other unstable component which may be used in another application. When the pregnancy test is to be performed, the rod 61 is depressed causing the piercing member 63 to rupture the membrane 65 thereby dispensing the powdered urea into the aqueous medium in the upper portion 36 of the syringe 19. The urea will quickly dissolve and the test can be immediately conducted in the manner described above. The piercing member 63 may also assist the dissolution of the powdered urea by causing a portion of it to be retained about the teeth 67 thereof. The retention aids in evenly distributing the powdered urea through the aqueous medium for rapid dissolution.

As mentioned above, syringes 18 and 19 may also be removable, and as such may have a body and outlet as shown in FIG. 1 for the syringe 17. This arrangement would be applicable when different wash solutions are required in the lower portions 37 of the syringes 18 and 19 since in the preferred device just described, such wash solutions are in communication with one another.

In its commercial form, the present device will be sold with a protective hard cover member 70 as shown in FIG. 1. The cover member 70 will fit snugly about a peripheral shoulder 71 about the bottom portion of the body 10 thereby protecting all of the components of the device prior to use. A projection (not shown) within the cover 70 may be desirable to plug the vent 51 while in storage thus preventing evaporation of wash solutions in the lower portions 37 of the syringes 18 and 19. Removal of the cover 70 unplugs the vent 51 in readiness for performance of the test.

While the embodiment of the invention described above and shown in FIGS. 1-3 provides a basic device for performing qualitative enzyme immunoassays cheaply and quickly, it has been found that occasionally false positive results may be obtained. The source of this problem has been found to reside in the failure of the wash solution in the lower portion 37 of the third syringe 19 (FIG. 1) to completely remove all traces of conjugate solution from the channel 41 and the outlet 31 of the syringe 18 (FIG. 2). This residual conjugate solution may subsequently contact the substrate solution as it is ejected from the third syringe 19. The resulting mixture seeps into the assay tube 11 where it causes a false positive reading.

Likewise, it has been found that contamination can occur from residual sample liquid persisting in the channel 40 and the opening 45 for the outlet 24 of the sample syringe 17. While this is probably of less seriousness to the effective operation of the device, it is conceivable that an erroneous result may be obtained if residual sample liquid can seep into contact with subsequently used reagents.

The use of built-in plungers 34 for the syringes 18 and 19 has been found to be disadvantageous from a practical point of view.

The plungers 34 must remain withdrawn from the syringes 18 and 19 until such time as the assay is to be conducted. Premature insertion of either plunger 34 will render the device useless. Also, packaging and transport of the device having extended plungers 34 requires the use of an oversized cover 70 (FIG. 1) which adds to the size of the device.

A further modification of the substrate syringe 19 for the situation where the substrate is a solid has been made to the second preferred embodiment. This modified syringe 19 is contained within the body 10 of the device and is felt to have certain advantages over the structure shown in FIG. 3.

As with the previous embodiment, the pregnancy assay for human chorionic gonadotropin (HCG) in urine will be used for illustrative purposes in describing the operation of this embodiment. FIG. 4 shows the second preferred embodiment of the invention having a body 100 and a centrally disposed assay tube 101 having applied to the inner wall thereof a coating of antibody suitable for the particular assay to be conducted. As with the previous embodiment, the tube 101 is connected in series to a plain uncoated tube 102 which acts as a control.

The device shown in FIG. 4 has a detachable sample syringe 110, a second syringe 111 containing enzyme/antibody conjugate solution, and a third syringe 112 containing enzyme substrate. The sample syringe 110 is insertable in the cylindrical receptacle 113 provided in the body 100. The syringe 110 has a plunger 116 (FIG. 5) having a piston 117 equipped with a central frustoconically shaped plug 118 which is snugly insertable into the frustoconically shaped hollow tip 119 of the syringe 110 so that the syringe opening 120 may be sealed to prevent seepage of any residual sample contained within the syringe 110.

The plunger 116 is hollowed out longitudinally and open at the top thereof so that a second plunger 125 may be stored therein during shipment and storage of the device. The plunger 125 is used to depress the pistons in the syringes 111 and 112 as will be described below.

Figure 6:
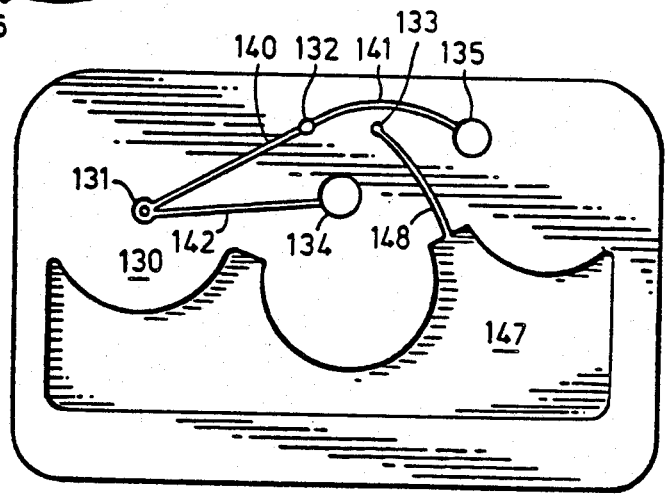
FIG. 6 shown on the same sheet as FIG. 8, is a plan view of the base of the second preferred device showing a more preferred circuitry for the liquid flows.

As shown in FIG. 6, this embodiment incorporates a modified circuitry for the flow of fluids from the syringes 110, 111 and 112 to the assay tube 101. The base 130 of the body 100 is provided with an opening 131 for receiving the tip 119 of the sample syringe 110, openings 132 and 133 for the tubes 101 and 102, and openings 134 and 135 for the second and third syringes 111 and 112. The openings 131 and 132 are connected by means of a channel 140 formed in the base 130, and openings 132 and 135 are connected by means of a channel 141. The opening 134 is indirectly connected to the opening 132 through a channel 142 running between openings 131 and 134. Finally, the opening 133 for the tube 102 is connected to a waste reservoir 147 by a channel 148.

This circuitry is used in conjunction with an improved upper piston 150 for the second syringe 111, as shown in FIG. 7, to solve the problem of false positive results obtained by contamination from residual conjugate solution remaining in the circuitry. As shown in FIG. 7 the syringe 111 has an upper piston 150 which comprises a structure having an upright wall 151 and a flanged bottom member 152. A flanged top cap 153 having a downward depending cylindrical wall 157 is inserted in the opening of the structure defined by the upright wall 151. The circuit circumferential edges of the flanged members 152 and 153 engage the cylindrical wall of the syringe 111. The piston wall 151 is provided with a plurality of small longitudinal grooves 155 spaced about the internal surface thereof and depending from corresponding notches 158 about the upper edge of the wall 151. These gooves 155 form liquid conduits between the piston wall 151 and the wall 157 of the top flanged member 153. Thus, the grooves 155 and notches 158 allow communication into the hollow interior of the piston 150 (see arrows 160). A central top vent structure 156 is provided in the top flanged member 153 and preferably comprises a frustoconical member extending inwardly as shown in FIG. 7.

The piston 150 operates in conjunction with the modified circuitry in the following fashion. After the sample liquid has passed through the assay tube 101 via the channel 140, the plunger 125 is applied to the upper piston 150 located near the top of the syringe 111. As in the previously described device, the syringe 111 is provided with a volume of wash solution in a lower portion 160 and an enzyme/antibody conjugate solution in an upper portion 161. The upper and lower portions 160 and 161 are separated by a piston 162. Pressure exerted by the plunger 125 on the upper piston 150 forces the wash solution from the lower portion 160 out the opening 134 and through the channels 142 and 140 to the opening 132. The channel 141 will already contain sample liquid a portion of which will be washed through the tube 101 along with the wash solution. Continued pressure on the piston 150 by means of the plunger 125 will cause the conjugate solution to flow from the upper portion 161 through the groove 165 in the wall of the syringe 111 as described above. In the present instance however, full travel of the upper piston 150 causes the edge of the lower flange member 152 to extend below the top of the groove 165 so that the interior of the piston 150 is in communication with the circuitry in the base 130 via the grooves 155 in the piston wall 151.

Figure 8:
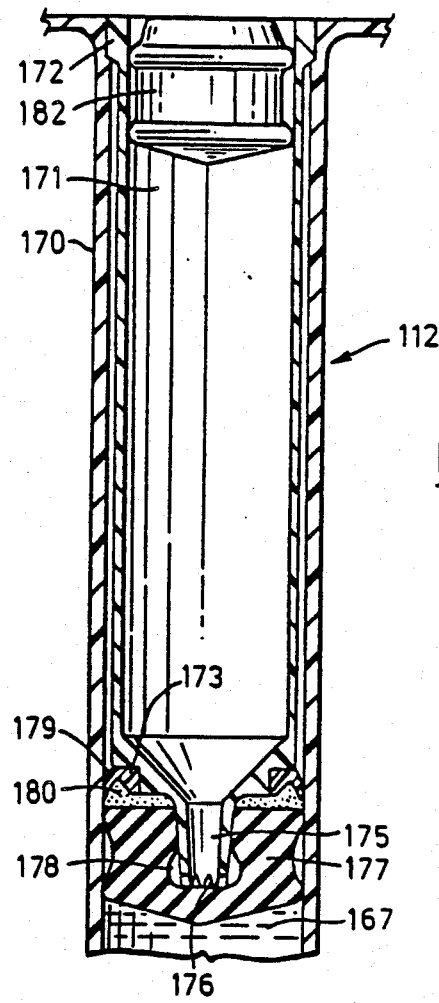
FIG. 8 is a sectional view of the details pertaining to an alternate third or substrate containing syringe.

The circuitry in the base 130 may at this point be purged of any extraneous sample and conjugate liquids by activation of the third syringe 112 with the plunger 125 forcing a second wash solution from a lower portion 167 thereof (FIG. 8). The wash solution from the syringe 112 proceeds through the opening 135 and the channel 141 to the opening 132 where it flows through the assay tube 101. At the same time was solution also proceeds along the channels 140 and 142 and through the opening 134, into the groove 165, past the flange 152 and up into the clearance between the outer wall of the piston 151 and the wall of the syringe 111 (arrows 160). After pressing through the notches 158 between the top of the piston wall 151 and the flanged cap 153, the liquid enters the interior of the piston 150 via conduits formed by the grooves 155 in the internal wall 151 of the piston 150. Control of the backflush mechanism just described is effected by adjusting the number, length and cross-sectional area of the conduits 155 formed in the piston 150. Thus, this arrangement of circuitry in the base 130 and the modified upper piston 150 in the syringe 111 eliminate the possibility of contamination of the substrate solution delivered from the third syringe 112 through the tube 101, thereby ensuring that false positive results cannot be obtained.

Finally, modifications to the construction of the third syringe 112 may be made as shown in FIG. 8. The cylindrical body 170 of the third syringe 112 comprises a lower portion 167 for the second wash solution and an upper syringe insert 171 containing substrate solvent and indicator. The syringe insert 171 has an outside diameter just less than the inside diameter of the bore of the syringe 112, and is provided with an upper rim 172 which engages the inner wall of the syringe 112 to make an interference fit therewith. That is, the insert 171 by virtue of the upper rim 172 is held in place within the cylindrical body 170 until it is used, at which time it can be forced down the bore of the syringe 112 by means of the plunger 125.

The insert 171 has a lower portion 173 which tapers frustoconically from the diameter of the body thereof to a lesser diameter cylindrical tip 175. The tip 175 has a castellated rim 176 and is inserted sealingly into a piston 177 provided with a cylindrical cavity 178 formed into the upper portion thereof for the purpose. The piston 177 forms the barrier between the wash solution in the lower portion 176 and the substrate and substrate solvent in the upper part of the syringe 112. The lower portion 173 of the insert 171 is provided with a circular flange 179 for engaging the inner wall of the syringe body 170. The space 180 defined between the top of the piston 177 and the flange 179 and the lower portion 173 of the insert 171 is used for storing substrate powder. The assembly of the syringe 112 is completed by capping the insert with a piston 182.

The operation of the syringe 112 is as follows. Pressure is exerted on the piston 182 of the insert 171 by means of the plunger 125 which, as mentioned above, was stored within the hollow sample syringe plunger 116 (FIG. 4). Hydraulic pressure from the piston 182 forces the lower piston 177 to pop off the tip 175 of the insert 171. Liquid comes out of the tip 175 forcing the piston 177 downward and causing the powdered substrate in the space 180 to dissolve therein. Upon full travel of the upper piston 182 to the bottom of the insert 171, continued pressure thereon by means of the plunger 125 causes the whole insert 171 to slide down the bore of the syringe 112. The substrate solution now in the lower portion 167 of the syringe 112 passes out through the opening 135 via a groove (not shown) in the wall of the syringe 112 as previously described.

The modified syringe 112 is designed to operate satisfactorily even when the sequence of events does not occur precisely as just described. Thus, initial pressure by the plunger 125 on the upper piston 182 may cause the insert to commence sliding down the bore of the syringe body 170. However, at the same time liquid from the insert 171 will be forced out through the castellated rim 176 of the tip 175, and this liquid will lubricate the surfaces of the tip 175 and piston 177 engaging one another thereby promoting disengagement of the piston 177 from the tip 175. Should the insert 171 travel the full length of the syringe 112 without disengagement of the piston 177 therefrom, continued pressure applied by the plunger 125 will force such disengagement and allow the final step of the assay to proceed.

I claim:

1. A device for performing an enzyme immunoassay, comprising:
   a body defining a receptacle including a first syringe containing a test liquid, and defining a second and a third syringe formed integrally in the body, the receptacle and syringes all having outlets;
   at least one assay tube being provided in the body, the tube having first and second ends and having an antibody, antigen or hapten attached to an internal surface of the tube;
   the body being provided with a flat bottom surface having grooves in it which connect outlets of the first, second and third syringes to the first end of the assay tube;
   a channel forming means being inserted over the bottom surface of the body, the means having a flat surface which coacts with the grooves to form channels for the flow of liquids from the syringes to the first end of the assay tube with the outlet of the second syringe being connected by a channel to the first end of the assay tube via the outlet of the first syringe; and
   the second and third syringes being each provided with first and second pistons spaced from one another, the second piston being directly depressed by a plunger, and each second and third syringe having a wall with a groove in it connecting the syringe outlet with the space above the first piston when it is fully depressed, the second syringe being provided with a first wash solution in the space defined therein below its first piston, and an enzyme conjugate containing solution in the space defined therein above its first piston; and the third syringe being provided with a second wash solution in the space defined therein below its first piston, and a solution containing enzyme substrate and enzyme metabolite indicator in the space defined therein above its first piston.

2. A device as claimed in claim 1, further comprising a control tube not having any antibody, antigen or hapten attached to its internal surface, the control tube being connected to one end of the assay tube.

3. A device as claimed in claim 1, further comprising a waste reservoir defined in the body for receiving and storing liquids which have flowed through the assay tube.

4. A device as claimed in claim 3, further comprising vent means for the reservoir and a protective hard cover for the device having means for plugging the vent means when the cover is in place.

5. A device as claimed in claim 1, wherein the third syringe is provided with a hollow plunger having a rod slidably disposed longitudinally within it, the rod having a piston affixed to its lower end, the piston being equipped with a piercing member protruding from the lower surface thereof, and the plunger having a rupture membrane covering an opening at its lower end; the membrane, the interior of the plunger and the lower end of the rod defining a chamber.

6. A device as claimed in claim 5, wherein human chorionic gonadotropin antibody (anti-HCG) is attached to the internal surface of the assay tube, the enzyme conjugate is urease/anti-HCG, the enzyme substrate is urea powder contained in the chamber, and the indicator is bromthymol blue.

7. A device as claimed in claim 1, wherein the second and third syringes are each provided with a rupture membrane about each outlet thereof to prevent cross contamination of solutions contained therein.

8. A device as claimed in claim 1, wherein the first syringe comprises a body having a frustoconically shaped hollow tip provided with an outlet for the syringe at its end, and a plunger having a frustoconically shaped plug on its end which is insertable into the tip so that it may be sealed.

9. A device as claimed in claim 1, wherein the second syringe has a second piston which comprises a hollow body having an upright wall with a flanged bottom member attached thereto, a flanged top member having a downward depending cylindrical wall is inserted into the opening defined by said upright wall, edges of said flanged members engage the wall of the syringe, the piston wall has at least one groove about its internal surface depending from one or more corresponding notches spaced about the upper edge of the piston wall, the grooves and notches forming conduits between the opposing walls of the piston and flanged top member to the interior of the piston; and a top vent structure extending inwardly from the top flanged member into the hollow body defining an opening through the member, the groove in the syringe wall being of sufficient height to extend above the bottom flange edge when the second piston is fully depressed.

10. A device as claimed in claim 9, wherein the vent structure extends into the hollow body approximately one-half its height.

11. A device as claimed in claim 1, wherein the third syringe has a syringe insert positioned in its upper portion to contain substrate solvent, the insert having a tip insertable into a cavity formed in the top of the first piston, the end of the insert and the top of the first piston defining a space to contain powdered substrate.

12. A device as claimed in claim 11, wherein the insert has an upper rim and a lower flange which slidably engage the wall of the syringe, the structure in between the rim and flange not touching the syringe wall.

13. A device as claimed in claim 11, wherein the tip of the insert is provided with a castellated edge.

14. A device as claimed in claim 1, wherein the outlet of the second syringe is connected to the first end of the assay tube by means of a channel running to the outlet for the first syringe and then to the first end of the assay tube, the third syringe outlet being connected directly to the first end of the assay tube by means of a channel.

* * * * *